United States Patent [19]
de Fraine et al.

[11] Patent Number: 5,432,197
[45] Date of Patent: * Jul. 11, 1995

[54] FUNGICIDAL PROPENOIC ACID DERIVATIVES

[75] Inventors: Paul J. de Fraine; Anne Martin, both of Wokingham, England

[73] Assignee: Zeneca Limited, London, England

[*] Notice: The portion of the term of this patent subsequent to Dec. 6, 2011 has been disclaimed.

[21] Appl. No.: 295,424

[22] Filed: Aug. 25, 1994

Related U.S. Application Data

[60] Continuation of Ser. No. 142,109, Oct. 28, 1993, Pat. No. 5,371,084, which is a continuation of Ser. No. 744,518, Aug. 13, 1991, abandoned, which is a division of Ser. No. 436,752, Nov. 15, 1989, Pat. No. 5,055,471.

[30] Foreign Application Priority Data

Mar. 9, 1988 [GB] United Kingdom ............... 8905383
Nov. 21, 1988 [GB] United Kingdom ............... 8827149

[51] Int. Cl.$^6$ ................... A61K 31/24; C07C 251/60
[52] U.S. Cl. .......................... 514/539; 560/35
[58] Field of Search ............. 560/35; 514/539

[56] References Cited

U.S. PATENT DOCUMENTS

| | | | |
|---|---|---|---|
| 4,773,034 | 2/1988 | Schirmer et al. | 560/60 |
| 4,829,085 | 5/1989 | Wendult et al. | 514/522 |
| 5,055,471 | 10/1991 | De Fraine et al. | 514/255 |
| 5,104,872 | 4/1992 | Tsubata et al. | 514/238.2 |
| 5,194,662 | 3/1993 | Brand et al. | 560/35 |
| 5,298,527 | 3/1994 | Grammenos et al. | 514/539 |
| 5,371,084 | 12/1994 | De Fraine et al. | 514/241 |

FOREIGN PATENT DOCUMENTS

| | | |
|---|---|---|
| 0024888 | 10/1981 | European Pat. Off. . |
| 0178826 | 4/1986 | European Pat. Off. . |
| 0203606 | 12/1986 | European Pat. Off. . |
| 0226917 | 7/1987 | European Pat. Off. . |
| 0230773 | 8/1987 | European Pat. Off. . |
| 0241901 | 10/1987 | European Pat. Off. . |
| 0251082 | 1/1988 | European Pat. Off. . |
| 0253313 | 1/1988 | European Pat. Off. . |

(List continued on next page.)

OTHER PUBLICATIONS

Chemical Abstracts, 92 (1980) 198103b.
Chemical Abstracts, 111 (1989) 92323u.

(List continued on next page.)

*Primary Examiner*—Richard L. Raymond
*Attorney, Agent, or Firm*—Cushman, Darby & Cushman

[57] ABSTRACT

Compounds having the formula (I):

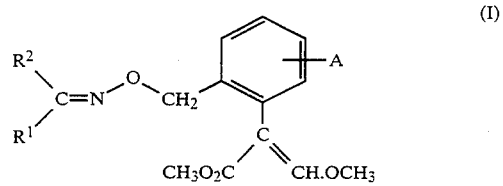

and stereoisomers thereof, wherein A is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$ and $R^2$, which may be the same or different, are hydrogen, optionally substituted alkyl, optionally substituted cycloalkyl, optionally substituted heterocyclylalkyl, optionally substituted cycloalkylalkyl, optionally substituted aralkyl, optionally substituted heteroarylalkyl, optionally substituted aryloxyalkyl, optionally substituted heteroaryloxyalkyl, optionally substituted alkenyl, optionally substituted alkynyl, optionally substituted alkoxy, optionally substituted aryl, optionally substituted heteroaryl, optionally substituted aryloxy, optionally substituted heteroaryloxy, nitro, halo, cyano, $-NR^3R^4$, $-CO_2R^3$, $-CONR^3R^4$, $-COR^3$, $-S(O)_nR^3$ wherein n is 0, 1 or 2, $(CH_2)_mPO(OR^3)_2$ wherein m is 0 or 1, or $R^1$ and $R^2$ join to form a carbocyclic or heterocyclic ring system; and $R^3$ and $R^4$, which may be the same or different, are hydrogen, optionally substituted alkyl, optionally substituted aralkyl, optionally substituted alkenyl, optionally substituted alkynyl, optionally substituted aryl or optionally substituted heteroaryl. The compounds are useful as fungicides, insecticides and miticides.

6 Claims, No Drawings

FOREIGN PATENT DOCUMENTS

| | | |
|---|---|---|
| 0273572 | 7/1988 | European Pat. Off. . |
| 2430416 | 1/1980 | France . |
| 2308330 | 9/1983 | Germany . |
| 3208330 | 9/1983 | Germany . |
| 1318681 | 5/1973 | United Kingdom . |
| WO90/07493 | 7/1990 | WIPO . |

OTHER PUBLICATIONS

Chemical Abstracts, 105 (1986) 78670z.
Chemical Abstracts, 107 (1987) 193307s.
Chemical Abstracts, 81 (1974) 22306d.
Chemical Abstracts, 107 (1987) 194794h.
Chemical Abstracts, vol. 114 (1990) 6032f.
Chemical Abstracts, vol. 115 (1991) 91848q.

FUNGICIDAL PROPENOIC ACID DERIVATIVES

This is a continuation of application Ser. No. 08/142,109, filed Oct. 28, 1993, now U.S. Pat. No. 5,371,084, which is a continuation of Ser. No. 07/744,518, filed Aug. 13, 1991, now abandoned, a division of Ser. No. 07/463,752, filed Nov. 15, 1989, now U.S. Pat. No. 5,055,471.

This invention relates to derivatives of propenoic acid useful as fungicides, insecticides and miticides, to processes for preparing them, to compositions containing them, and to methods of using them to combat fungi, especially fungal infections of plants, and to kill or control insects and mites.

According to the present invention there is provided a compound having the formula (I):

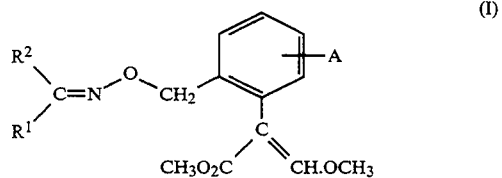

and stereoisomers thereof, wherein A is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$ and $R^2$, which may be the same or different, are hydrogen, optionally substituted alkyl, optionally substituted cycloalkyl, optionally substituted heterocyclylalkyl, optionally substituted cycloalkylalkyl, optionally substituted aralkyl, optionally substituted heteroarylalkyl, optionally substituted aryloxyalkyl, optionally substituted heteroaryloxyalkyl, optionally substituted alkenyl, optionally substituted alkynyl, optionally substituted alkoxy, optionally substituted aryl, optionally substituted heteroaryl, optionally substituted aryloxy, optionally substituted heteroaryloxy, nitro, halo, cyano, $-NR^3R^4$, $-CO_2R^3$, $-CONR^3R^4$, $-COR^3$, $-S(O)_nR^3$ wherein n is 0, 1 or 2, $(CH_2)_mPO(OR^3)_2$ wherein m is 0 or 1, or $R^1$ and $R^2$ join to form a carbocyclic or heterocyclic ring system; and $R^3$ and $R^4$ which may be the same or different, are hydrogen, optionally substituted alkyl, optionally substituted aralkyl, optionally substituted alkenyl, optionally substituted alkynyl, optionally substituted aryl or optionally substituted heteroaryl.

The compounds of the invention contain at least one carbon-nitrogen double bond and at least one carbon-carbon double bond, and are sometimes obtained in the form of mixtures of geometric isomers. However these mixtures can be separated into individual isomers, and this invention embraces such isomers, and mixtures thereof in all proportions.

The individual isomers which result from the unsymmetrically substituted double bond of the propenoate group and the oxime are identified by the commonly used terms "E" and "Z". These terms are defined according to the Cahn-Ingold-Prelog system which is fully described in the literature (see, for example, J March, "*Advanced Organic Chemistry*, 3rd edition, Wiley-Interscience, page 109 et seq).

For the carbon-carbon double bond of the propenoate group, usually one isomer is more active fungicidally than the other, the more active isomer usually being the one wherein the group $-CO_2CH_3$ and $-OCH_3$ are on opposite sides of the olefinic bond of the propenoate group (the (E)-isomer). These (E)-isomers form a preferred embodiment of this invention.

Halo includes fluoro, chloro, bromo and iodo.

Alkyl and the alkyl moieties of alkoxy, aralkyl and aryloxyalkyl can be in the form of straight or branched chains and, unless otherwise stated, suitably contain from 1 to 6 carbon atoms. Examples are methyl, ethyl, iso-propyl and tert-butyl. Optional substituents include halo (especially chloro and fluoro), hydroxy and $C_{1-4}$ alkoxy. Examples of substituted alkyl and substituted alkoxy are trifluoromethyl and trifluoromethoxy.

Cycloalkyl is suitably $C_{3-6}$ cycloalkyl, for example cyclopropyl and cyclohexyl, and cycloalkylalkyl is suitably $C_{3-6}$ cycloalkyl($C_{1-4}$)alkyl, for example cyclopropylethyl.

Alkenyl and alkynyl suitably contain from 2 to 6 carbon atoms, typically 2 to 4 carbon atoms, in the form of straight or branched chains. Examples are ethenyl, allyl and propargyl. Substituted alkenyl and alkynyl groups include optionally substituted arylalkenyl (especially optionally substituted phenylethenyl) and arylalkynyl.

Aryl and the aryl moieties of aralkyl, arylalkenyl, arylalkynyl, aryloxy and aryloxyalkyl include phenyl and naphthyl.

The carbocyclic or heterocyclic ring system which $R^1$ and $R^2$ may form together is suitably a $C_{5-10}$ aliphatic, aromatic or mixed aliphatic/aromatic carbocyclic ring system, for example cyclopentyl, cyclohexyl, cyclohexadienonyl and such groups carrying a fused benzene ring and/or substituents such as methyl; or it may be a 5- to 10-membered heterocyclic ring system, for example tetrahydropyranyl.

The term heteroaryl is used to described aromatic heterocyclic groups. Heteroaryl and heterocyclyl and the heteroaryl and heterocyclyl moieties of other groups, such as heteroaryloxyalkyl and heterocyclylalkyl, are typically 5- or 6-membered rings containing one or more O, N or S heteroatoms which may be fused to one or more other aromatic, heteroaromatic or heterocyclic rings such as a benzene ring. Examples are thienyl, furyl, pyrrolyl, triazolyl, thiazolyl, pyridyl, pyrimidinyl, pyrazinyl, pyridazinyl, triazinyl, quinolinyl and quinoxalinyl groups and N-oxides thereof.

Substitutents which may be present in optionally substituted aryl and heteroaryl moieties include one or more of the following: halo, hydroxy, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridyl or pyrimidinyl), optionally substituted aryloxy (especially optionally substituted phenoxy), optionally substituted heteroaryloxy (especially optionally substituted pyridyloxy or pyrimidinyloxy), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridyl- or pyrimidinyl($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridylethenyl or pyrimidinylethenyl), optionally substituted aryl($C_{1-4}$)alkoxy (especially optionally substituted benzyloxy), optionally substituted heteroaryl($C_{1-4}$)alkoxy (especially optionally substituted pyridyl-, or pyrimidinyl($C_{1-4}$)alkoxy), optionally substituted aryloxy($C_{1-4}$)alkyl (especially phenoxymethyl), optionally substituted heteroaryloxy($C_{1-4}$)alkyl (especially optionally substituted pyridyloxy- or pyrimidinyloxy($C_{1-4}$)alkyl ), acyloxy, including $C_{1-4}$ alkanoyloxy (especially acetyloxy) and benzoyloxy, cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Substituents which may be present in the aryl or heteroaryl rings of any of the foregoing substituents include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —SO$_2$R", —OSO$_2$R', —COR', —CR'NR" or —N=CR'R" in which R' and R" have the meanings given above.

In one aspect the invention includes a compound of formula (I) wherein A is hydrogen, halo, hydroxy, methyl, methoxy, trifluoromethyl, trifluoromethoxy, $C_{1-2}$ alkylcarbonyl, $C_{1-2}$ alkoxycarbonyl, phenoxy, nitro or cyano; $R^1$ is $C_{1-4}$ alkyl, halo($C_{1-4}$)alkyl, $C_{1-4}$ alkoxy, halo($C_{1-4}$)alkoxy, $C_{1-4}$ alkylcarbonyl, $C_{1-4}$ alkoxycarbonyl, cyano, phenyl($C_{1-4}$)alkyl, phenyl, a 5- or 6-membered aromatic heterocycle containing one or more O, N or S atoms and optionally fused to a benzene ring, the aromatic or heteroaromatic moieties of any of the foregoing being optionally substituted with one or more of halo, hydroxy, $C_{1-4}$ alkyl, halo($C_{1-4}$)alkyl, $C_{1-4}$ alkoxy, halo($C_{1-4}$)alkoxy, $C_{1-4}$ alkylcarbonyl, $C_{1-4}$ alkoxycarbonyl, nitro, cyano, phenyl, phenoxy, benzyl or benzyloxy; and $R^2$ is hydrogen, halo, $C_{1-4}$ alkyl, halo($C_{1-4}$)alkyl, $C_{1-4}$ alkylcarbonyl, $C_{1-4}$ alkoxycarbonyl, cyano or phenyl; or $R^1$ and $R^2$ join together to form a $C_{5-10}$ carbocyclic ring system.

In another aspect the invention includes a compound of formula (I) wherein A is hydrogen or halo; $R^1$ is $C_{1-4}$ alkyl, benzyl, $C_{1-4}$ alkylcarbonyl, $C_{1-4}$ alkoxycarbonyl, cyano, phenyl, thienyl, triazolyl, thiazolyl, pyridyl, pyrimidinyl, pyrazinyl, pyridazinyl, triazinyl, quinolinyl or quinoxalinyl, the aromatic or heteroaromatic moieties of any of the foregoing being optionally substituted with one or more of halo, $C_{1-4}$ alkyl, trifluoromethyl, $C_{1-4}$ alkoxy, trifluoromethoxy, nitro, cyano, phenyl or benzyloxy; and $R^2$ is hydrogen, $C_{1-4}$ alkyl, $C_{1-4}$ alkylcarbonyl, $C_{1-4}$ alkoxycarbonyl, cyano or phenyl; or $R^1$ and $R^2$ join together to form a cyclopentyl or cyclohexyl ring to which is optionally fused a benzene ring.

This invention is illustrated by the compounds listed in Table I which follows. Throughout Table I the methyl 3-methoxypropenoate group has the (E)-configuration.

TABLE I

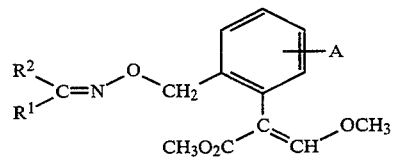

| COMPOUND NO. | $R^1$ | $R^2$ | A | OXIME* | OLEFINIC+ | MELTING POINT, °C. | ISOMER RATIO++ |
|---|---|---|---|---|---|---|---|
| 1 | 2-CH$_3$O—C$_6$H$_4$ | H | H | 8.50 | 7.60 | Oil | |
| 2 | 3-CH$_3$O—C$_6$H$_4$ | H | H | 8.05 | 7.60 | Oil | |
| 3 | 4-CH$_3$O—C$_6$H$_4$ | H | H | | | | |
| 4 | 2-CH$_3$—C$_6$H$_4$ | H | H | | | | |
| 5 | 3-CH$_3$—C$_6$H$_4$ | H | H | 8.05 | 7.59 | Oil | |
| 6 | 4-CH$_3$—C$_6$H$_4$ | H | H | 8.07 | 7.60 | Oil | 19:1 |
| 7 | 2-F-C$_6$H$_4$ | H | H | | | | |
| 8 | 3-F—C$_6$H$_4$ | H | H | | | | |
| 9 | 4-F—C$_6$H$_4$ | H | H | | | | |
| 10 | 2-Cl—C$_6$H$_4$ | H | H | | | | |
| 11 | 3-Cl—C$_6$H$_4$ | H | H | 8.04 | 7.59 | Oil | |
| 12 | 4-Cl—C$_6$H$_4$ | H | H | | | | |
| 13 | 2-Br—C$_6$H$_4$ | H | H | | | | |
| 14 | 3-Br—C$_6$H$_4$ | H | H | | | | |
| 15 | 4-Br—C$_6$H$_4$ | H | H | | | | |
| 16 | 2-NO$_2$—C$_6$H$_4$ | H | H | | | | |
| 17 | 3-NO$_2$—C$_6$H$_4$ | H | H | 8.14 | 7.61 | Oil | |
| 18 | 4-NO$_2$—C$_6$H$_4$ | H | H | | | | |
| 19 | 2-CF$_3$—C$_6$H$_4$ | H | H | | | | |
| 20 | 3-CF$_3$—C$_6$H$_4$ | H | H | 8.12 | 7.60 | Oil | |
| 21 | 4-CF$_3$—C$_6$H$_4$ | H | H | | | | |
| 22 | C$_6$H$_5$ | H | H | 8.10 | 7.60 | 63-6 | |
| 23 | C$_6$H$_5$ | CH$_3$ | H | | 7.59 | Oil | |
| 24 | C$_6$H$_5$ | C$_6$H$_5$ | H | | | | |
| 25 | 2-C$_6$H$_5$—C$_6$H$_4$ | H | H | | | | |
| 26 | 3-C$_6$H$_5$—C$_6$H$_4$ | H | H | | | | |

TABLE I-continued

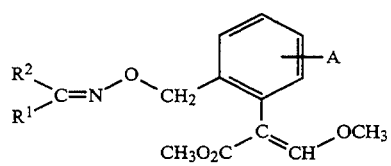

| COMPOUND NO. | R[1] | R[2] | A | OXIME* | OLEFINIC+ | MELTING POINT, °C. | ISOMER RATIO++ |
|---|---|---|---|---|---|---|---|
| 27 | 4-C$_6$H$_5$—C$_6$H$_4$ | H | H | | | | |
| 28 | 2-(C$_6$H$_5$CH$_2$O)—C$_6$H$_4$ | H | H | | | | |
| 29 | 3-(C$_6$H$_5$CH$_2$O)—C$_6$H$_4$ | H | H | 8.06 | 7.60 | Oil | |
| 30 | 4-(C$_6$H$_5$CH$_2$O)—C$_6$H$_4$ | H | H | | | | |
| 31 | 2-cyano-C$_6$H$_4$ | H | H | | | | |
| 32 | 3-cyano-C$_6$H$_4$ | H | H | 8.07 | 7.60 | Oil | |
| 33 | 4-cyano-C$_6$H$_4$ | H | H | | | | |
| 34 | 2-CF$_3$O—C$_6$H$_4$ | H | H | | | | |
| 35 | 3-CF$_3$O—C$_6$H$_4$ | H | H | | | | |
| 36 | 4-CF$_3$O—C$_6$H$_4$ | H | H | | | | |
| 37 | pyrid-2-yl | H | H | 8.19 | 7.60 | Oil | |
| 38 | pyrid-3-yl | H | H | 8.10 | 7.60 | Oil | |
| 39 | pyrid-4-yl | H | H | 8.03 | 7.61 | 110.5–111.5 | |
| 40 | pyrid-2-yl | CH$_3$ | H | | 7.60 | Oil | |
| 41 | pyrid-2-yl | cyano | H | | 7.63 | 144–6 | |
| 42 | pyrid-2-yl | CO$_2$C$_2$H$_5$ | H | | 7.56 | Oil | |
| 43 | pyrid-2-yl | CO$_2$CH$_3$ | | | | | |
| 44 | pyrimidin-2-yl | H | H | | | | |
| 45 | pyrimidin-4-yl | H | H | 8.07 | 7.61 | 96–9 | |
| 46 | thien-2-yl | H | H | | | | |
| 47 | thien-2-yl | CH$_3$ | H | | 7.58 | Oil | 16:1 |
| 48 | 5-Cl-thien-2-yl | H | H | | | | |
| 49 | CO$_2$C$_2$H$_5$ | CO$_2$C$_2$H$_5$ | H | | 7.58 | Oil | |
| 50 | CO$_2$CH$_3$ | CO$_2$CH$_3$ | H | | | | |
| 51 | COCH$_3$ | COCH$_3$ | H | | | | |
| 52 | cyano | cyano | H | | | | |
| 53 | φ | φ | H | | | | |
| 54 | φ | φ | H | | | | |
| 55 | φ | φ | H | | 7.58 | Oil | |
| 56 | tert-C$_4$H$_9$ | H | H | | | | |
| 57 | C$_6$H$_5$CH$_2$ | H | H | | | | |
| 58 | 2,4-di-Cl—C$_6$H$_3$ | H | H | | | | |
| 59 | 2,4-di-F—C$_6$H$_3$ | H | H | | | | |
| 60 | 3,5-di-CH$_3$—C$_6$H$_3$ | H | H | | | | |
| 61 | 3,5-di-CH$_3$O—C$_6$H$_3$ | H | H | | | | |
| 62 | pyrazin-2-yl | CH$_3$ | H | | 7.61 | 116–118.5 | |
| 63 | 6-CH$_3$-pyrid-3-yl | CH$_3$ | H | | 7.60 | 67–73 | |
| 64 | pyrid-2-yl | C$_2$H$_5$ | H | | 7.60 | 70–80 | |
| 65 | pyrid-3-yl | CH$_3$ | H | | 7.60 | Oil | 24:1 |
| 66 | pyrimidin-5-yl | iso-C$_3$H$_7$ | H | | 7.60 | Oil | |
| 67 | iso-C$_3$H$_7$ | pyrimidin-5-yl | H | | 7.53 | Oil | |
| 68 | pyrid-4-yl | CH$_3$ | H | | | | |
| 69 | 6-Cl-pyrid-2-yl | CH$_3$ | H | | | | |
| 70 | 5-Cl-pyrid-2-yl | CH$_3$ | H | | | | |
| 71 | 4-Cl-pyrid-2-yl | CH$_3$ | H | | | | |
| 72 | 3-Cl-pyrid-2-yl | CH$_3$ | H | | | | |
| 73 | 6-cyano-pyrid-2-yl | CH$_3$ | H | | | | |
| 74 | 5-cyano-pyrid-2-yl | CH$_3$ | H | | | | |
| 75 | 4-cyano-pyrid-2-yl | CH$_3$ | H | | 7.61 | 98-99 | |
| 76 | 3-cyano-pyrid-2-yl | CH$_3$ | H | | | | |
| 77 | 6-Br-pyrid-2-yl | CH$_3$ | H | | | | |
| 78 | 5-Br-pyrid-2-yl | CH$_3$ | H | | | | |
| 79 | 4-Br-pyrid-2-yl | CH$_3$ | H | | | | |
| 80 | 3-Br-pyrid-2-yl | CH$_3$ | H | | | | |
| 81 | 6-CH$_3$-pyrid-2-yl | CH$_3$ | H | | | | |
| 82 | 5-CH$_3$-pyrid-2-yl | CH$_3$ | H | | | | |
| 83 | 4-CH$_3$-pyrid-2-yl | CH$_3$ | H | | | | |
| 84 | 3-CH$_3$-pyrid-2-yl | CH$_3$ | H | | | | |
| 85 | 6-F-pyrid-2-yl | CH$_3$ | H | | | | |
| 86 | 5-F-pyrid-2-yl | CH$_3$ | H | | | | |
| 87 | 4-F-pyrid-2-yl | CH$_3$ | H | | | | |
| 88 | 3-F-pyrid-2-yl | CH$_3$ | H | | | | |
| 89 | 3-CH$_3$-pyrazin-2-yl | CH$_3$ | H | | 7.60 | 106–8 | |
| 90 | 3-C$_2$H$_5$-pyrazin-2-yl | CH$_3$ | H | | 7.59 | 74–76.5 | |
| 91 | 3-Cl-pyrazin-2-yl | CH$_3$ | H | | | | |
| 92 | 3-OCH$_3$-pyrazin-2-yl | CH$_3$ | H | | 7.58 | Oil | |
| 93 | 5-CO$_2$CH$_3$-pyrazin-2-yl | CH$_3$ | H | | 7.60 | Oil | 4:1 |
| 94 | 5-CO$_2$C$_2$H$_5$-pyrazin-2-yl | CH$_3$ | H | | | | |
| 95 | 3-cyano-pyrazin-2-yl | CH$_3$ | H | | | | |
| 96 | pyrimidin-4-yl | CH$_3$ | H | | | | |
| 97 | 2-Cl-pyrimidin-4-yl | CH$_3$ | H | | | | |

TABLE I-continued $$R^2\!-\!C(R^1)\!=\!N\!-\!O\!-\!CH_2\!-\!\text{(phenyl-A)}\!-\!C(CO_2CH_3)\!=\!CH\!-\!OCH_3$$

| COMPOUND NO. | R¹ | R² | A | OXIME* | OLEFINIC+ | MELTING POINT, °C. | ISOMER RATIO++ |
|---|---|---|---|---|---|---|---|
| 98 | 2-OCH₃-pyrimidin-4-yl | CH₃ | H | | | | |
| 99 | 2-CH₃-pyrimidin-4-yl | CH₃ | H | | | | |
| 100 | 2-cyano-pyrimidin-4-yl | CH₃ | H | | | | |
| 101 | thiazol-2-yl | CH₃ | H | | 7.60 | 107–114 | 10:1 |
| 102 | thien-3-yl | CH₃ | H | | 7.60 | Oil | |
| 103 | 5-Cl-thien-2-yl | CH₃ | H | | | | |
| 104 | 5-CH₃-thien-2-yl | CH₃ | H | | | | |
| 105 | 5-Br-thien-2-yl | CH₃ | H | | | | |
| 106 | 5-cyano-thien-2-yl | CH₃ | H | | | | |
| 107 | 3-CH₃-thien-2-yl | CH₃ | H | | | | |
| 108 | 2-OCH₃—C₆H₄ | CH₃ | H | | 7.57 | Oil | |
| 109 | 3-OCH₃—C₆H₄ | CH₃ | H | | | | |
| 110 | 4-OCH₃-C₆H₄ | CH₃ | H | | 7.57 | 85–7 | |
| 111 | 2-CH₃—C₆H₄ | CH₃ | H | | 7.58 | Oil | |
| 112 | 3-CH₃—C₆H₄ | CH₃ | H | | 7.58 | Oil | |
| 113 | 4-CH₃—C₆H₄ | CH₃ | H | | 7.58 | Oil | |
| 114 | 2-F—C₆H₄ | CH₃ | H | | 7.59 | Oil | |
| 115 | 3-F—C₆H₄ | CH₃ | H | | 7.60 | Oil | |
| 116 | 4-F—C₆H₄ | CH₃ | H | | 7.59 | Oil | |
| 117 | 2-Cl—C₆H₄ | CH₃ | H | | | | |
| 118 | 3-Cl—C₆H₄ | CH₃ | H | | 7.59 | Oil | |
| 119 | 4-Cl—C₆H₄ | CH₃ | H | | | | |
| 120 | 2-Br—C₆H₄ | CH₃ | H | | | | |
| 121 | 3-Br—C₆H₄ | CH₃ | H | | 7.59 | Oil | |
| 122 | 4-Br—C₆H₄ | CH₃ | H | | | | |
| 123 | 2-NO₂—C₆H₄ | CH₃ | H | | 7.59 | 70–72 | |
| 124 | 3-NO₂—C₆H₄ | CH₃ | H | | | | |
| 125 | 4-NO₂—C₆H₄ | CH₃ | H | | 7.60 | 100–2 | |
| 126 | 2-CF₃—C₆H₄ | CH₃ | H | | | | |
| 127 | 3-CF₃—C₆H₄ | CH₃ | H | | 7.60 | Oil | |
| 128 | 4-CF₃—C₆H₄ | CH₃ | H | | | | |
| 129 | 2-cyano-C₆H₄ | CH₃ | H | | | | |
| 130 | 3-cyano-C₆H₄ | CH₃ | H | | 7.60 | 75.5–77 | |
| 131 | 4-cyano-C₆H₄ | CH₃ | H | | 7.59 | Oil | |
| 132 | 3,4,5-(OCH₃)₃-C₆H₂ | CH₃ | H | | | | |
| 133 | 3,5-di-F-pyrid-2-yl | CH₃ | H | | | | |
| 134 | 3,4,5,6-F₄-pyrid-2-yl | CH₃ | H | | | | |
| 135 | 2,6-di-Cl-pyrid-3-yl | CH₃ | H | | | | |
| 136 | pyridazin-3-yl | CH₃ | H | | | | |
| 137 | pyridazin-4-yl | CH₃ | H | | | | |
| 138 | 6-CH₃-pyridazin-3-yl | CH₃ | H | | | | |
| 139 | 4-cyano-quinolin-2-yl | CH₃ | H | | 7.63 | 160.5–162 | |
| 140 | quinoxalin-2-yl | CH₃ | H | | 7.62 | 179–181 | |
| 141 | C₆H₅ | CH₃ | 6-F | | | | |
| 142 | C₆H₅ | CH₃ | 6-Cl | | | | |
| 143 | 6-CH₃-pyrimidin-4-yl | CH₃ | H | | 7.60 | Oil | 4:1 |
| 144 | 4-CH₃-pyrimidin-5-yl | CH₃ | H | | 7.58 | Oil | 6:1 |
| 145 | 4-CH₃-pyrimidin-2-yl | CH₃ | H | | 7.57 | Oil | |
| 146 | 4,6-di-CH₃-pyrimidin-2-yl | CH₃ | H | | | | |
| 147 | 2,6-di-CH₃-pyrimidin-4-yl | CH₃ | H | | | | |
| 148 | 2,4-di-CH₃-pyrimidin-5-yl | CH₃ | H | | | | |
| 149 | 6-Cl-pyrimidin-4-yl | CH₃ | H | | | | |
| 150 | 6-OCH₃-pyrimidin-4-yl | CH₃ | H | | | | |
| 151 | 4,6-di-OCH₃-pyrimidin-2-yl | CH₃ | H | | | | |
| 152 | φ | φ | H | | 7.58 | Oil | |
| 153 | φ | φ | H | | 7.58 | 109–110 | |
| 154 | N-oxide-pyrid-2-yl | CH₃ | H | | 7.52 | Oil | |
| 155 | 5-C₂H₅-pyrid-2-yl | CH₃ | H | | 7.59 | 78 | |
| 156 | CH₃CO | CH₃ | H | | 7.59 | 78 | |
| 157 | C₆H₅CO | CH₃ | H | | 7.56 | 55 | |
| 158 | N-CH₃-pyrrol-2-yl | CH₃ | H | | 7.57 | Oil | |
| 159 | 4-Cl-quinolin-2-yl | CH₃ | H | | 7.62 | 114–116 | |
| 160 | 2,4-di-Cl—C₆H₃ | 1,2,4-triazol-1-yl-CH₂ | H | | 7.61 | Oil | |
| 161 | 2,4-di-Cl—C₆H₃ | pyrid-3-yl-CH₂ | H | | | | |
| 162 | 2,4-di-CH₃-thiazol-5-yl | CH₃ | H | | 7.58 | Oil | |
| 163 | furan-2-yl | CH₃ | H | | 7.58 | Oil | |
| 164 | 2,4-di-CH₃-furan-3-yl | CH₃ | H | | | | |
| 165 | pyrid-2-yl | pyrid-2-yl | H | | 7.56 | Oil | |
| 166 | 6-C₆H₅-pyrimidin-4-yl | CH₃ | H | | | | |

TABLE I-continued $$R^2\underset{R^1}{\overset{}{>}}C=N-O-CH_2-\underset{CH_3O_2C}{\overset{}{>}}\underset{CH}{\overset{}{>}}C=CH-OCH_3 \quad A$$

| COMPOUND NO. | R[1] | R[2] | A | OXIME* | OLEFINIC[+] | MELTING POINT, °C. | ISOMER RATIO[++] |
|---|---|---|---|---|---|---|---|
| 167 | 4-cyano-pyrid-3-yl | CH$_3$ | H | | | | |
| 168 | 1,2,4-triazin-5-yl | CH$_3$ | H | | | | |
| 169 | 3-CH$_3$-1,2,4-triazin-5-yl | CH$_3$ | H | | | | |
| 170 | 3-C$_6$H$_5$-1,2,4-triazin-5-yl | CH$_3$ | H | | | | |
| 171 | 3-SCH$_3$-1,2,4-triazin-5-yl | CH$_3$ | H | | | | |
| 172 | 3-OCH$_3$-1,2,4-triazin-5-yl | CH$_3$ | H | | | | |
| 173 | 5-CONH$_2$-pyrazin-2-yl | CH$_3$ | H | | 7.60 | 146–8 | 3:1 |
| 174 | 5-cyano-pyrazin-2-yl | CH$_3$ | H | | 7.62 | 89–92 | |
| 175 | 5,6-di-CH$_3$-pyrazin-2-yl | CH$_3$ | H | | 7.60 | 114–6 | |
| 176 | 3,5-di-CH$_3$-pyrazin-2-yl | CH$_3$ | H | | 7.59 | 56–60 | 7:3 |
| 177 | 3,6-di-CH$_3$-pyrazin-2-yl | CH$_3$ | H | | 7.59 | Oil | |
| 178 | 5-CH$_3$-pyrazin-2-yl | CH$_3$ | H | | | | |
| 179 | 6-CH$_3$-pyrazin-2-yl | CH$_3$ | H | | | | |
| 180 | 5-Cl-pyrazin-2-yl | CH$_3$ | H | | | | |
| 181 | 6-Cl-pyrazin-2-yl | CH$_3$ | H | | | | |
| 182 | 5,6-dicyano-pyrazin-2-yl | CH$_3$ | H | | | | |
| 183 | 4-SO$_2$CH$_3$—C$_6$H$_4$ | CH$_3$ | H | | 7.59 | Oil | |
| 184 | 4-NH$_2$—C$_6$H$_4$ | CH$_3$ | H | | 7.58 | Oil | |
| 185 | 2,4-di-Cl—C$_6$H$_3$ | CH$_3$ | H | | 7.60 | 79–82 | |
| 186 | 2,4-di-CH$_3$—C$_6$H$_3$ | CH$_3$ | H | | 7.57 | 66–68.5 | |
| 187 | 4-NHCONH$_2$—C$_6$H$_4$ | CH$_3$ | H | | | | |
| 188 | C$_6$H$_5$ | cyclopropyl | H | | 7.57 | Oil | 8:1 |
| 189 | C$_6$H$_5$ | Cl | H | | | | |
| 190 | 4-C$_2$H$_5$O—C$_6$H$_4$ | CF$_3$ | H | | 7.55 | Oil | |
| 191 | C$_6$H$_5$ | SCH$_3$ | H | | 7.57 | Oil | |
| 192 | C$_6$H$_5$ | F | H | | | | |
| 193 | C$_6$H$_5$ | OC$_2$H$_5$ | H | | | | |
| 194 | C(CH$_3$)$_3$ | CH$_3$ | H | | 7.57 | Oil | |
| 195 | cyclohexyl-CH$_2$ | CH$_3$ | H | | | | |
| 196 | C$_6$H$_5$—CH$_2$ | CH$_3$ | H | | 7.57 | Oil | |
| 197 | pyrazin-2-yl-CH$_2$ | CH$_3$ | H | | | | |
| 198 | (E)-C$_6$H$_5$—CH=CH | CH$_3$ | H | | 7.58 | Oil | |
| 199 | C$_6$H$_5$—OCH$_2$ | CH$_3$ | H | | | | |
| 200 | C$_6$H$_5$ | CH$_2$Cl | H | | | | |
| 201 | benzthiazol-2-yl | CH$_3$ | H | | | | |
| 202 | benzoxazol-2-yl | CH$_3$ | H | | | | |
| 203 | pyrazin-2-yl | C$_2$H$_5$ | H | | | | |
| 204 | 5-OCH$_3$-pyrazin-2-yl | CH$_3$ | H | | | | |
| 205 | 6-OCH$_3$-pyrazin-2-yl | CH$_3$ | H | | | | |
| 206 | 6-cyano-pyrazin-2-yl | CH$_3$ | H | | | | |
| 207 | 5-cyano-pyrid-3-yl | CH$_3$ | H | | | | |
| 208 | 6-cyano-pyrid-3-yl | CH$_3$ | H | | | | |
| 209 | 3-cyano-pyrid-4-yl | CH$_3$ | H | | | | |
| 210 | 2-cyano-pyrid-4-yl | CH$_3$ | H | | | | |
| 211 | pyrimidin-5-yl | CH$_3$ | H | | | | |
| 212 | 2-CH$_3$-pyrimidin-5-yl | CH$_3$ | H | | | | |
| 213 | 3-OCH$_3$-isoxazol-5-yl | CH$_3$ | H | | | | |
| 214 | 3-Br-isoxazol-5-yl | CH$_3$ | H | | | | |
| 215 | 5-NO$_2$-thiazol-2-yl | CH$_3$ | H | | | | |
| 216 | 5-CH$_3$-thiazol-2-yl | CH$_3$ | H | | | | |
| 217 | 4-CH$_3$-thiazol-5-yl | CH$_3$ | H | | | | |
| 218 | 2-Cl,4-CH$_3$-thiazol-5-yl | CH$_3$ | H | | | | |
| 219 | 3,5-di-OCH$_3$-1,2,4-triazin-6-yl | CH$_3$ | H | | | | |
| 220 | 3,6-di-CH$_3$-pyridazin-4-yl | CH$_3$ | H | | | | |
| 221 | 2-(C$_6$H$_5$O)—C$_6$H$_4$ | CH$_3$ | H | | | | |
| 222 | 3-(C$_6$H$_5$O)—C$_6$H$_4$ | CH$_3$ | H | | | | |
| 223 | 4-(C$_6$H$_5$O)—C$_6$H$_4$ | CH$_3$ | H | | | | |
| 224 | 1,2,4-triazol-1-yl-CH$_2$ | CH$_3$ | H | | | | |
| 225 | C$_6$H$_5$ | OCH$_3$ | H | | 7.53 | Gum | |
| 226 | OCH$_3$ | C$_6$H$_5$ | H | | 7.58 | Gum | |
| 227 | C$_6$H$_5$ | CH$_3$S(O) | H | | 7.60 | Gum | |
| 228 | C$_6$H$_5$ | CH$_3$S(O)$_2$ | H | | 7.60 | Gum | |
| 229 | C$_6$H$_5$ | N(CH$_3$)$_2$ | H | | | | |
| 230 | C$_6$H$_5$O | CH$_3$ | H | | | | |
| 231 | C$_6$H$_5$ | Br | H | | | | |
| 232 | C$_6$H$_5$ | I | H | | | | |
| 233 | C$_6$H$_5$ | | | | | | |
| 234 | Pyrimidin-2-yl | | | | | | |

TABLE I-continued

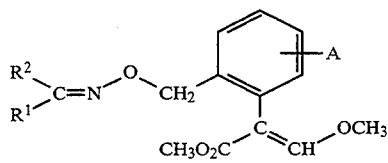

| COMPOUND NO. | R¹ | R² | A | OXIME* | OLEFINIC+ | MELTING POINT, °C. | ISOMER RATIO++ |
|---|---|---|---|---|---|---|---|
| 235 | Pyrazin-2-yl | | Cl | H | | | |

Key
+Chemical shift of singlet from olefinic proton on β-methoxypropenoate group of major oxime ether isomer (ppm from tetramethylsilane).
*Chemical shift of singlet from the proton on aldoxime, where appropriate.
++Of isomers resulting from the unsymmetrically substituted oxime double bond.
φGroup R¹ and R² join to form a ring as follows:
Compound 53 is:

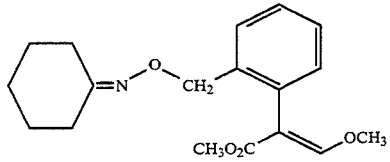

Compound 54 is:

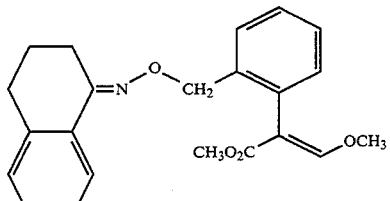

Compound 55 is:

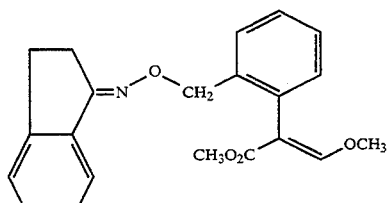

Compound 152 is:

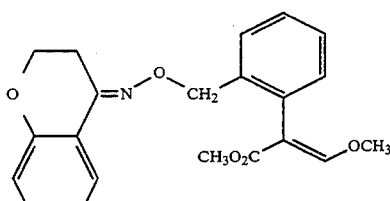

Compound 153 is:

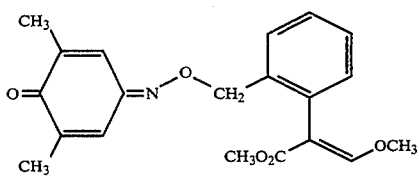

TABLE II

SELECTED PROTON NMR DATA

TABLE II shows selected proton NMR data for certain compounds described in Table I. Chemical shifts are measured in ppm from tetramethylsilane, and deuterochloroform was used as solvent throughout. The column headed 'frequency' refers to the operating frequency of the NMR spectrometer. The following abbreviations are used:

TABLE II-continued

SELECTED PROTON NMR DATA br = broad
s = singlet
d = doublet
t = triplet
q = quartet
m = multiplet TABLE II-continued

SELECTED PROTON NMR DATA

| COMPOUND NO. | FREQUENCY MHz | |
|---|---|---|
| 1 | 270 | 3.69(3H, s), 3.82(3H, s), 3.83(3H, s), 5.12(2H, s), 6.84–6.99(2H, m), 7.11–7.2(1H, m), 7.25–7.4(3H, m), 7.5–7.62(1H, m), 7.60(1H, s), 7.74–7.8(1H, m), 8.50(1H, s) ppm. |
| 2 | 400 | 3.70(3H, s), 3.80(3H, s), 3.81(3H,s), 5.13(2H, s), 6.9–7.54(8H, m), 7.60(1H, s) ppm. |
| 6 | 270 | (major isomer) 2.36(3H, s), 3.68(3H, s), 3.80(3H, s), 5.10(2H, s), 7.1–7.5(8H, m), 7.60(1H, s), 8.07(1H, s) ppm. |
| 11 | 270 | 3.70(3H, s), 3.81(3H, s), 5.14(2H, s), 7.15–7.20(1H, m), 7.24–7.43(5H, m), 7.48–7.54(1H, m), 7.58–7.62(1H, m), 7.59(1H, s), 8.04(1H, s) ppm. |
| 17 | 270 | 3.70(3H, s), 3.84(3H, s), 5.17(2H, s), 7.16–7.22(1H, m), 7.32–7.39(2H, m), 7.49–7.58(2H, m), 7.60(1H, s), 7.88(1H, d), 8.14(1H, s), 8.17–8.23(1H, m), 8.42(1H, m) ppm. |
| 20 | 270 | 3.70(3H, s), 3.83(3H, s), 5.16(2H, s), 7.14–7.20(1H, m), 7.31–7.38(2H, m), 7.46–7.55(2H, m), 7.55–7.64(1H, m), 7.60(1H, s), 7.7–7.77(1H, d), 7.83(1H, s), 8.12(1H, s) ppm. |
| 23 | 270 | 2.25(3H, s), 3.69(3H, s), 3.81(3H, s), 5.16(2H, s), 7.13–7.20(1H, m), 7.3–7.4(5H, m), 7.5–7.55(1H, m), 7.59(1H, s), 7.6–7.66(2H, m) ppm. |
| 29 | 270 | 3.68(3H, s), 3.80(3H, s), 5.08 (2H, s), 5.13(2H, s), 6.94–7.07(1H, m), 7.07–7.56(12H, m), 7.60(1H, s), 8.06(1H, s) ppm. |
| 32 | 270 | 3.70(3H, s), 3.83(3H, s), 5.14(2H, s), 7.1–7.9(8H, m), 7.60(1H, s), 8.07(1H, s) ppm. |
| 37 | 270 | 3.69(3H, s), 3.81(3H, s), 5.18(2H, s), 7.16–7.82(7H, m), 7.60(1H, s), 8.19(1H, m), 8.6(1H, m) ppm. |
| 38 | 270 | 3.69(3H, s), 3.82(3H, s), 5.14(2H, s), 7.14–7.53(5H, m), 7.601H, s), 7.90–7.96(1H, m), 8.10(1H, s), 8.55–8.62(1H, m), 8.72(1H, m) ppm. |
| 40 | 270 | 2.34(3H, s), 3.69(3H, s), 3.81(3H, s), 5.19(2H, s), 7.1–7.7(6H, m), 7.60(1H, s), 7.89(1H, d), 8.59(1H, d) PPM. |
| 42 | 270 | 1.32–1.40(3H, t), 3.63(3H, s), 3.77(3H, s), 4.33–4.44(2H, q), 5.25(2H, s), 7.13–7.20(1H, m), 7.26–7.42(4H, m), 7.56(1H, s), 7.7–7.77(2H, m), 7.66–7.71(1H, m) ppm. |
| 47 | 270 | 2.24(3H, s), 3.69(3H, s), 3.82(3H, s), 5.11(2H, s), 6.9–7.55(7H, m), 7.58(3H, s) ppm. |
| 49 | 270 | 1.3(6H, q), 3.70(3H, s), 3.83(3H, s), 4.36(4H, q), 5.28(2H, s), 7.1–7.5(4H, m), 7.58(1H, s) ppm. |
| 55 | 270 | 2.85–3.12(4H, m), 3.69(3H, s), 3.82(3H, s), 5.14(2H, s), 7.1–7.7(8H, m), 7.58(1H, s) ppm. |
| 65 | 270 | (major isomer) 2.24(3H, s), 3.68(3H, s), 3.81(3H, s), 5.16(2H, s), 7.1–7.5(5H, m), 7.60(1H, s), 7.9(1H, m), 8.57(1H, m), 8.83(1H, m) ppm. |
| 66 | 270 | 1.22(6H, d), 3.57(1H, m), 3.69(3H, s), 3.82(3H, s), 5.13(2H, s), 7.1–7.5(4H, m), 7.60(1H, s), 8.81(2H, s), 9.18(1H, s) ppm. |
| 67 | 270 | 1.14(6H, d), 2.83(1H, m), 3.66(3H, s), 3.78(3H, s), 5.00(2H, s), 7.1–7.4(4H, m), 7.53(1H, s), 8.66(2H, s), 9.17(1H, s) ppm. |
| 92 | 270 | 2.26( 3H, s), 3.68(3H, s), 3.80(3H, s), 4.00(3H, s), 5.21(3H, s), 7.1–7.6(4H, m), 7.58(1H, s), 8.08(1H, d), 8.16(1H, d) ppm. |
| 93 | 270 | (major isomer) 2.30(3H, s), 3.69(3H, s), 3.83(3H, s), 4.03(3H, s), 5.24(2H, s), 7.1–7.55(4H, m), 7.60(1H, s), 9.20(1H, m), 9.23(1H, m), (minor isomer) 2.30(3H, s), 3.64(3H, s), 3.80(3H, s), 4.03(3H, s), 5.12(2H, s), 7.1–7.55(4H, m), 7.57(1H, s), 9.32(1H, m), 9.37(1H, m) ppm. |
| 102 | 270 | 2.22(3H, s), 3.68(3H, s), 3.83(3H, s), 5.12(2H, s), 7.15–7.55(7H, m), 7.60(1H, s) ppm. |
| 108 | 270 | 2.20(3H, s), 3.67(3H, s), 3.80(3H, s), 3.83(3H, s), 5.14(2H, s), 6.87–7.60(8H, m), 7.57(1H, s) ppm. |
| 111 | 270 | 2.20(3H, s), 2.30(3H, s), 3.68(3H, s), 3.80(3H, s), 5.13(2H, s), 7.15–7.4(7H, m), 7.54(1H, m), 7.58(1H, s) ppm. |
| 112 | 270 | 2.23(3H, s), 2.37(3H, s), 3.68(3H, s), 3.81(3H, s), 5.16(2H, s), 7.1–7.55(8H, m), 7.58(1H, s) ppm. |
| 113 | 270 | 2.22(3H, s), 2.35(3H, s), 3.68(3H, s), 3.81(3H, s), 5.13(3H, s), 7.1–7.5(8H, m), 7.58(1H, s) ppm. |
| 114 | 270 | 2.26(3H, s), 3.68(3H, s), 3.81(3H, s), 5.16(2H, s), 7.0–7.55(8H, m), 7.59(1H, s) ppm. |
| 115 | 270 | 2.02(3H, s), 3.68(3H, s), 3.82(3H, s), 5.15(2H, s), 7.0–7.55(8H, m), 7.60(1H, s) ppm. |
| 116 | 270 | 2.22(3H, s), 3.68(3H, s), 3.82(3H, s), 5.13(2H, s), 6.99–7.65(8H, m), 7.59(1H, s) ppm. |
| 118 | 270 | 2.21(3H, s), 3.69(3H, s), 3.81(3H, s), 5.16(2H, s), 7.14–7.66(8H, m), 7.59(1H, s) ppm. |
| 121 | 270 | 2.21(3H, s), 3.69(3H, s), 3.82(3H, s), 5.16(2H, s), 7.1–7.55(7H, m), 7.59(1H, s), 7.81(1H, m) ppm. |
| 127 | 270 | 2.26(3H, s), 3.69(3H, s), 3.83(3H, s), 5.18(2H, s), 7.15–7.92(8H, m), 7.60(1H, s) ppm. |
| 131 | 270 | 2.22(3H, s), 3.68(3H, s), 3.82(3H, s), 5.18(2H, s), 7.1–7.8(8H, m), 17.59(1H, s) ppm. |
| 143 | 270 | (major isomer) 2.28(3H, s), 2.53(3H, s), 3.69(3H, s), 3.83(3H, s), 5.22(2H, s), 7.1–7.5(4H, m), 7.60(1H, s), 7.72(1H, s), 9.06(1H, s) ppm. (minor isomer) 2.27(3H, s), 2.48(3H, s), 3.69(3H, s), 3.83(3H, s), 5.21(2H, s), 7.1≃7.5(4H, m), 7.61(1H, s), 7.77(1H, s), 9.10(1H, s) ppm. |
| 144 | 270 | (major isomer) 2.22(3H, s), 2.50(3H, s), 3.67(3H, s), 3.81(3H, s), 5.14(2H, s), 7.1–7.5(4H, m), 7.58(1H, s), 8.53(1H, s), 9.02(1H, s) ppm. (minor isomer) 2.17(3H, s), 2.40(3H, s), 3.65(3H, s), 3.77(3H, s), 5.00(2H, s), 7.1–7.5(4H, m), 7.52(1H, s), 8.37(1H, s), 9.05(1H, s) ppm. |
| 145 | 270 | 2.39(3H, s), 2.57(3H, s), 3.68(3H, s), 3.81(3H, s), 5.33(2H, s), 7.11(1H, d), 7.1–7.55(4H, m), 7.57(1H, s), 8.64(1H, d) ppm. |
| 152 | 270 | 2.92(2H, t), 3.68(3H, s), 3.82(3H, s), 4.18(2H, t), 5.14(2H, s), 6.8–7.0(2H, m), 7.1–7.5(5H, m), 7.58(1H, s), 7.87(1H, m) ppm. |
| 154 | 270 | 2.22(3H, s), 3.61(3H, s), 3.75(3H, s), 5.08(2H, s), 7.0–7.5(7H, m), 7.52(1H, s), 8.12(1H, m) ppm. |
| 158 | 270 | 2.08(3H, s), 3.67(6H, s), 3.80(3H, s), |

TABLE II-continued

SELECTED PROTON NMR DATA

| | | |
|---|---|---|
| | | 5.06(2H, s), 6.08(1H, m), 6.38(1H, m), 6.06(1H, m), 7.1-7.5(4H, m), 7.57(1H, s) ppm. |
| 160 | 270 | 3.69(3H, s), 3.82(3H, s), 5.19(2H, s), 5.42(2H, s), 7.1-7.5(7H, m), 7.61(1H, s), 7.77(1H, s), 8.05(1H, s) ppm. |
| 162 | 270 | 2.21(3H, s), 2.46(3H, s), 2.62(3H, s), 3.68(3H, s), 3.82(3H, s), 5.10(2H, s), 7.1-7.5(4H, m), 7.58(1H, s) ppm. |
| 163 | 270 | 2.16(3H, s), 3.68(3H, s), 3,81(3H, s), 5.17(2H, s), 6.42(1H, m), 6.61(1H, m), 7.1-7.55(6H, m), 7.58(1H, s) ppm. |
| 165 | 270 | 3.63(3H, s), 3.76(3H, s), 5.22(2H, s), 7.1-7.8(10H, m), 7.56(1H, s), 8.55(1H, d), 8.70(1H, d) ppm. |
| 177 | 270 | 2.29(3H, s), 2.51(3H, s), 2.53(3H, s), 3.68(3H, s), 3.81(3H, s), 5.15(2H, s), 7.1-7.5(4H, m), 7.59(1H, s), 8.24(1H, s) ppm. |
| 183 | 270 | 2.24(3H, s), 3.03(3H, s), 3.68(3H, s), 3.82(3H, s), 5.20(2H, s), 7.1-7.5(4H, m), 7.59(1H, s), 7.8-8.0(4H, m) ppm. |
| 184 | 270 | 2.18(3H, s), 3.67(3H, s), 3.78(3H, s), 3.80(2H, br.s), 5.11(2H, s), 6.59(2H, d), 7.1-7.55(6H, m), 7.58(1H, s) ppm. |
| 188 | 270 | (major isomer) 0.65(2H, m), 0.90(2H, m), 2.32(1H, m), 3.67(3H, s), 3.80(3H, s), 5.13(2H, s), 7.1-7.6(9H, m), 7.57(1H, s) ppm. (minor isomer) 0.65(2H, m), 2.32(1H, m), 3.63(3H, s), 3.76(3H, s), 4.97(2H, s), 7.1-7.6(9H, m), 7.77(1H, s) ppm. |
| 190 | 270 | 1.41(3H, t), 3.64(3H, s), 3.76(3H, s), 4.05(2H, q), 5.18(2H, s), 6.8-7.55(8H, m), 7.55(1H, s) ppm. |
| 191 | 270 | 2.04(3H, s), 3.66(3H, s), 3.78(3H, s), 5.19(2H, s), 7.1-7.4(8H, m), 7.5-7.6(1H, m), 7.57(1H, s) ppm. |
| 194 | 270 | 1.10(9H, s), 1.81(3H, s), 3.68(3H, s), 3.81(3H, s), 4.99(2H, s), 7.1-7.5(4H, m), 7.57(1H, s) ppm. |
| 196 | 270 | 1.76(3H, s), 3.46(2H, s), 3.67(3H, s), 3.80(3H, s), 5.06(2H, s), 7.1-7.5(9H, m), 7.57(1H, s) ppm. |
| 198 | 270 | 2.10(3H, s), 3.69(3H, s), 3.82(3H, s), 5.11(2H, s), 6.85(2H, s), 7.1-7.5(9H, m), 7.58(1H, s) ppm. |
| 225 | 270 | 3.60(3H, s), 3.70(3H, s), 3.78(3H, s), 4.94(2H, s), 7.1-7.5(7H, m), 7.53(1H, s), 7.77-7.81(2H, m) ppm. |
| 226 | 270 | 3.66(3H, s), 3.77(3H, s), 3.98(3H, s), 5.04(2H, s), 7.10-7.58(7H, m), 7.58(1H, s), 7.60-7.70(2H, m) ppm. |
| 227 | 270 | 2.88(3H, s), 3.67(3H, s), 3.79(3H, s), 5.18(2H, dd), 7.1-7.5(7H, m), 7.60(1H, s), 7.6-7.7(2H, m) ppm. |
| 228 | 270 | 3.20(3H, s), 3.67(3H, s), 3.80(3H, s), 5.30(2H, s), 7.1-7.6(9H, m), 7.60(1H, s) ppm. |

The compounds of the invention of formula (I) may be prepared by the step shown in Scheme 1. The terms A, $R^1$ and $R^2$ are as defined above and X is a leaving group such as halogen (chlorine, bromine or iodine).

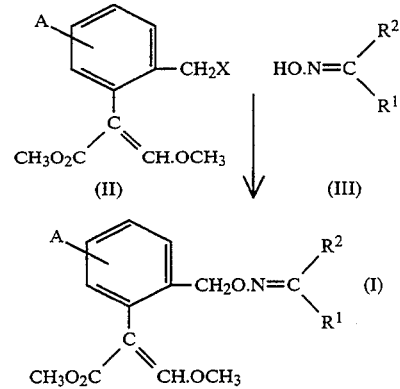

Scheme 1

The compounds of formula (I) may be prepared by treating oximes of general formula (III) with a suitable base (such as sodium hydride or sodium methoxide), in a suitable solvent (such as N,N-dimethylformamide or tetrahydrofuran), to form the anion and then adding a compound of formula (II).

Oximes of the general formula (III) are well known in the chemical literature. The compound of general formula (II) where X is bromine and the propenoate group has the (E)-configuration is described in EP-A-0203606.

Alternatively compounds of the invention of formula (I) may be prepared by the steps shown in Scheme 2. The terms A, $R^1$, $R^2$ and X are as defined above, $R^5$ is hydrogen or a metal (such as sodium or potassium), L is a leaving group such as a halide (chloride, bromide or iodide), a $CH_3SO_4$ anion, or a sulphonyl anion. Each transformation is performed at a suitable temperature and usually, though not always, in a suitable solvent.

The compounds of the invention of formula (I) can be prepared from phenylacetates of formula (VI) or the ketoesters of formula (X) by the steps shown in Scheme 2.

Thus compounds of formula (I) can be prepared by treatment of phenylacetates of formula (VI) with a base (such as sodium hydride or sodium methoxide) and methyl formate. If a species of formula $CH_3L$, wherein L is as defined above, is then added to the reaction mixture, compounds of formula (I) may be obtained. If a protic acid is added to the reaction mixture, compounds of formula (IX), wherein $R^5$ is hydrogen, are obtained. Alternatively the species of formula (IX), wherein $R^5$ is a metal (such as sodium), may themselves be isolated from the reaction mixture.

Compounds of formula (IX), wherein $R^5$ is a metal, can be converted into compounds of formula (I) by treatment with a species $CH_3L$, wherein L is as defined above. Compounds of formula (IX), wherein $R^5$ is hydrogen, can be converted into compounds of formula (I) by successive treatment with a base (such as potassium carbonate) and a species of general formula $CH_3L$.

Alternatively, compounds of formula (I) can be prepared from acetals of formula (IV) by elimination of methanol under either acidic or basic conditions. Examples of reagents or reagent mixtures which can be used for this transformation are lithium di-isopropylamide; potassium hydrogen sulphate (see, for example, T Yamada, H Hagiwara and H Uda, *J. Chem. Soc. Chemical Communications*, Scheme 2

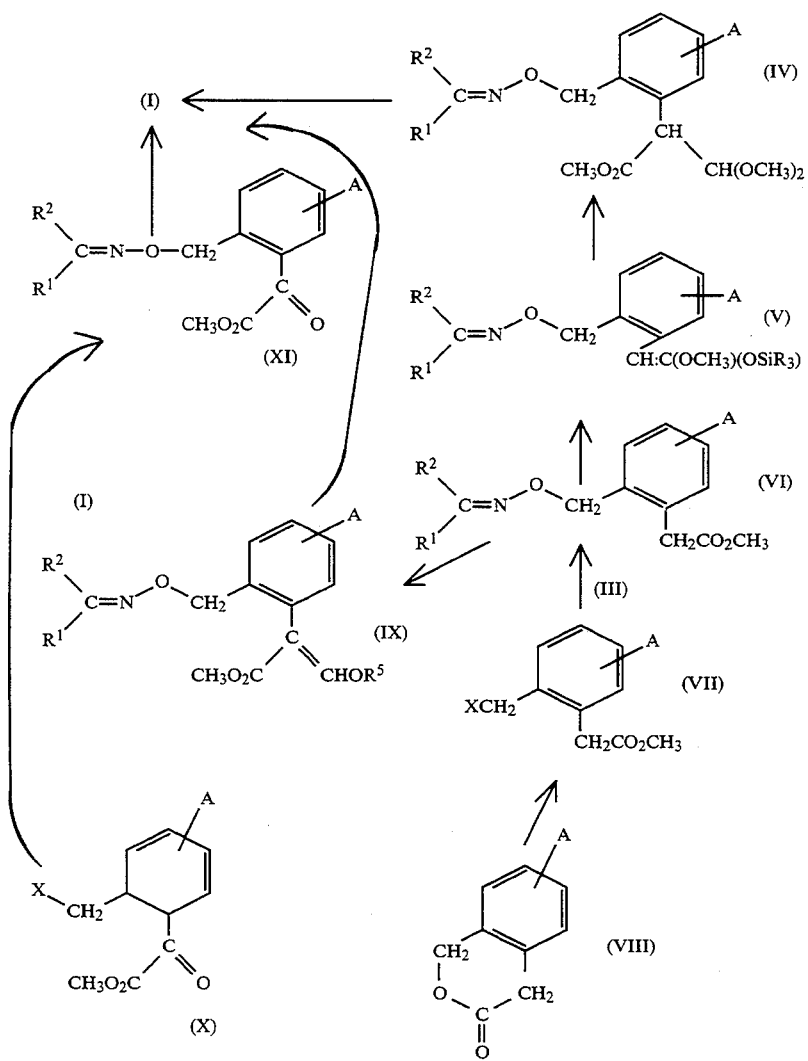

1980, 838, and references therein); and triethylamine often in the presence of a Lewis acid such as titanium tetrachloride (see, for example, K. Nsunda and L. Heresi, *J. Chem. Soc. Chemical Communications*, 1985, 1000).

Acetals of formula (IV) can be prepared by treatment of methyl silyl ketene acetals of formula (V), wherein R is an alkyl group, with trimethyl orthoformate in the presence of a Lewis acid such as titanium tetrachloride (see, for example, K. Saigo, M. Osaki and T. Mukaiyama, *Chemistry Letters*, 1976, 769).

Methyl silyl ketene acetals of formula (V) can be prepared from phenylacetates of formula (VI) by treatment with a base and trialkylsilyl halide of formula $R_3SiCl$ or $R_3SiBr$, such as trimethylsilyl chloride, or a base (such as triethylamine) and a trialkylsilyl triflate of formula $R_3Si-OSO_2CF_3$ (see, for example, C. Ainsworth, F. Chen and Y. Kuo, *J. Organometallic Chemistry*, 1972, 46, 59).

It is not always necessary to isolate the intermediates (IV) and (V); under appropriate conditions compounds of formula (I) may be prepared from phenylacetates of formula (VI) in "one pot" by the successive addition of suitable reagents listed above.

Phenylacetates of formula (VI) may be prepared from phenylacetates of formula (VII). Thus, if an oxime of general formula (III) is treated with a suitable base (such as sodium hydride or sodium methoxide) and the phenyl acetates of formula (VII) are added, phenylacetates of formula (VI) are obtained.

Phenylacetates of formula (vII) are obtained from isochromanones of formula (VIII) by treatment with HX, wherein X is a halogen (such as bromine), in methanol. This transformation may also be accomplished in 2 steps if the isochromanone (VIII) is treated with HX in a non-alcoholic solvent, and the resulting phenylacetic acid is then esterified using standard procedures (see, for example, I. Matsumoto and J. Yoshizawa, Jpn. Kokai (Tokkyo Koho) 79 138 536, 27.10.1979, *Chem. Abs.*, 1980, 92, 180829h; and G. M. F. Lim, Y. G. Perron and R. D. Droghini, *Res. Discl.*, 1979, 188, 672, *Chem. Abs.*, 1980, 92, 128526t). Isochromanones of formula (VIII) are well known in the chemical literature.

Alternatively, compounds of formula (I) can be prepared by treatment of ketoesters of formula (XI) with methoxymethylenation reagents such as methoxymethylenetriphenylphosphorane (see, for example, W. Steglich, G. Schramm, T. Anke and F. Oberwinkler, EP 0044 448, 4.7.1980).

Ketoesters of formula (XI) may be prepared from ketoesters of formula (X), by treatment with the anion of oximes of general formula (III) as described above. Ketoesters of formula (X) are described in EP 0331 061.

The compounds of the invention are active fungicides and may be used to control one or more of the following pathogens:

*pyricularia oryzae* on rice.

*Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines.

Helminthosporium spp., Rhynchosporium spp., Septoria spp., Pyrenophora spp., *Pseudocercosporella herpotrichoides* and *Gaeumannomyces graminis* on cereals.

*Cercospora arachidicola* and *Cercosporidium personata* on peanuts and other Cercospora species on other hosts, for example, sugar beet, bananas, soya beans and rice.

*Botrytis cinerea* (grey mould) on tomatoes, strawberries, vegetables, vines and other hosts.

Alternaria spp. on vegetables (e.g. cucumber), oil-seed rape, apples, tomatoes and other hosts.

Venturia inaequalis (scab) on apples.

Plasmopara viticola on vines.

Other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits. *Phytophthora infestans* on potatoes and tomatoes and other Phytopthora spp. on vegetables, strawberries, avocado, pepper, ornamentals, tobacco, cocoa and other hosts. *Thanatephorus cucumeris* on rice and other Rhizoctonia species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and Botrytis cinerea on grapes).

Further, some of the compounds may be active as seed dressings against Fusarium spp., Septoria spp., Tilletia spp., (bunt, a seed-borne disease of wheat), Ustilago spp. and Helminthosporium spp. on cereals, Rhizoctonia solani on cotton and *Pyricularia oryzae* on rice.

The compounds may have systemic movement in plants. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

Some of the compounds exhibit insecticidal activity and, at appropriate rates of application, may be used to combat a range of insects and mites.

Therefore in another aspect of the invention there is provided a method of killing or controlling insects or mites which comprises administering to the insect or mite or to the locus thereof an insecticidally or miticidally effective amount of a compound as hereinbefore defined or a composition containing the same.

The compounds may be used directly for agricultural purposes but are more conveniently formulated into compositions using a carrier or diluent. The invention thus provides fungicidal, insecticidal and miticidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments. The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used. The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are ($\pm$)-2-(2,4-dichlorophenyl)-3-(1H-1,2,4-triazol-1-yl)propyl 1,1,2,2-tetrafluoroethyl ether, (RS)-1-aminopropylphosphonic acid, (RS)-4-(4-chlorophenyl)-2-phenyl-2-(1H-1,2,4-triazol-1-ylmethyl)butyronitrile, (RS)-4-chloro-N-(cyano(ethoxy)methyl)benzamide, (Z)-N-but-2-enyloxymethyl-2-chloro-2',6'-diethylacetanilide, 1-(2-cyano-2-methoxyiminoacetyl)-3-ethyl urea, 1-[2RS,4RS;2RS,4RS)-4-bromo-2-(2,4-dichlorophenyl)-tetrahydrofurfuryl]-1H-1,2,4-triazole, 3-(2,4-dichlorophenyl)-2-(1H-1,2,4-triazol-1-yl)quinazolin-4(3H)-one, 3-chloro-4-[4-methyl-2-(1H-1,2,4-triazol-1-methyl)-1,3-dioxolan-2-yl]phenyl-4-chlorophenyl ether, 4-bromo-2-cyano-N,N-di-methyl-6-trifluoromethylbenzimidazole-1-sulphonamide, 4-chlorobenzyl N-(2,4-dichlorophenyl)-2-(1H-1,2,4-triazol-1-yl)thioacetamidate, 5-ethyl-5,8-dihydro-8-oxo(1,3)-dioxolo(4,5-g)quinoline-7-carboxylic acid, $\alpha$-[N-(3-chloro-2,6-xylyl)-2-methoxyacetamido]-$\gamma$-butyrolactone, anilazine, BAS 454, benalaxyl, benomyl, biloxazol, binapacryl, bitertanol, blasticidin S, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, dimethamorph, dimethirimol, diniconazole, dinocap, ditalimfos, dithianon, dodemorph, dodine, edifenphos, etaconazole, ethirimol, ethyl (Z)-N-benzyl-N-([methyl-(methylthioethylideneamino-oxycarbonyl)amino]-thio)-$\beta$-alaninate, etridiazole, fenapanil, fenarimol, fenfuram, fenpiclonil, fenpropidin, fenpropimorph, fentin acetate, fentin hydroxide, flutolanil, flutriafol, fluzilazole, folpet, fosetylaluminium, fuberidazole, furalaxyl, furconazole-cis, guazatine, hexaconazole, hydroxyisoxazole, imazalil, iprobenfos, iprodione, isoprothiolane, kasugamycin, mancozeb, maneb, mepronil, metalaxyl, methfuroxam, metsulfovax, myclobutanil, neoasozin, nickel dimethyldithiocarbamate, nitrothal-isopropyl, nuarimol, ofurace, organomercury compounds, oxadixyl, oxycarboxin, penconazole, pencycuron, pent-4-enyl N-furfuryl-N-imidazol-1-ylcarbonyl-DL-homoalaninate, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, techlofthalam, tecnazene, tebuconazole, thiabendazole, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-di-methyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. GA$_3$, GA$_4$ or GA$_7$) and triapenthenol.

The following Examples illustrate the invention. Throughout the Examples, the term 'ether' refers to diethyl ether, magnesium sulphate was used to dry solutions, and solutions were concentrated under reduced pressure. Reactions involving air or water sensitive intermediates were performed under an atmosphere of nitrogen and solvents were dried before use, where appropriate. Unless otherwise stated, chromatography was performed on a column of silica gel as the stationary phase. Where shown, infrared and NMR data are selective; no attempt is made to list every absorption in all cases. $^1$H NMR spectra were recorded using CDCl$_3$-solutions unless otherwise stated. The following abbreviations are used throughout:

| | | | |
|---|---|---|---|
| THF | = tetrahydrofuran | s | = singlet |
| DMF | = N,N-dimethylformamide | d | = doublet |
| NMR | = nuclear magnetic resonance | t | = triplet |
| IR | = infrared | m | = multiplet |
| m.p. | = melting point | br | = broad |
| HPLC | = high performance liquid chromatography. | | |

EXAMPLE 1

This Example illustrates the preparation of (E),(E)-methyl 3-methoxy-2-[2-(3-methylbenzaldoximinomethyl)phenyl]propenoate (Compound No. 5 of Table I).

A solution of (E)-3-methylbenzaldoxime (0.23 g) in DMF (5 ml) was added dropwise to a stirred suspension of sodium hydride (0.051 g) in DMF (5 ml) at room temperature. After ½ hour, a solution of (E)-methyl 2-[2-(bromomethyl)phenyl]-3-methoxypropenoate (0.5 g, prepared by the method described in EP-A-0203606) in DMF (5 ml) was added to the reaction mixture, which was then stirred at room temperature for 4 hours. The mixture was poured into water and extracted (×2) with ether. The combined extracts were washed with water, then dried, concentrated and chromatographed using ether as the eluant to give the title compound (0.132 g, 23% yield) as a pale yellow oil.

IR maxima (film): 1709, 1631 cm$^{-1}$. $^1$H NMR (270 MHz) δ: 2.35 (3H, s); 3.69 (3H, s); 3.80 (3H, s); 5.12 (2H, s); 7.1–7.55 (8H, m); 7.59 (1H, s); 8.05 (1H, s) ppm.

EXAMPLE 2

This Example illustrates the preparation of the (E),(E) and (Z),(E) mixture of methyl 2-[2-(3,5-di-methylpyrazin-2-yl-acetoximinomethyl)phenyl]-3-methoxypropenoate (Compound No. 176 of Table I).

To a mixture of 2,6-dimethylpyrazine (3.24 g), sulfuric acid (15 ml of a 3.4M solution) and acetaldehyde (10 ml), stirred at 0° C., was added simultaneously a solution of ferrous sulphate (50.1 g in 150 ml of water) and t-butylhydroperoxide (16.2 ml of a 70% aqueous solution). The temperature during the addition was kept below 3° C. After the addition the reaction mixture was stirred at 0° C. for 1 hour. Sodium metabisulphate was added until the mixture gave a negative starch-iodine test. The reaction mixture was extracted with dichloromethane, the combined extracts were washed with water, then dried, concentrated and chromatographed using a mixture of ether and 60°–80° C. petrol (4:1) as the eluant, to give 2-acetyl-3,5-di-methylpyrazine (2.65 g, 59% yield) as a pale yellow oil.

IR maxima (film): 1694, 1551, 1262, 1175 cm$^{-1}$. $^1$H NMR (270 MHz) δ: 2.62(3H,s), 2.70(3H,s), 2.80(3H,s), 8.36(1H,s) ppm.

2-Acetyl-3,5-dimethylpyrazine (2.65 g), hydroxylamine hydrochloride (2.5 g) and sodium acetate trihydrate (3.5 g) were refluxed in methanol (50 ml) for 1 hour. The reaction mixture was concentrated, diluted with water (75 ml) and extracted with ethyl acetate. The combined extracts were dried and concentrated to give an oil which was triturated with ether and 60°–80° C. petrol to give 3,5-dimethyl-2-(1-hydroximinoethyl)-pyrazine (2.54 g, 87% yield) as a white solid (m.p. 85°–89° C.) and as a 1:1 mixture of (E/Z) isomers.

IR maxima (film): 2925, 1465, 1376, 1086, 930 cm$^{-1}$. $^1$H NMR (270 MHz) δ: 2.23(3H,s), 2.33(3H,s), 2.53(3H,s), 2.56(3H,s), 2.58(3H,s), 2.68(3H,s), 8.32(1H,s), 8.35(1H,s), 9.45(1H,br.s), 9.85(1H,br.s) ppm.

A 1:1 mixture of (E/Z)-3,5-dimethyl-2-(1-hydroximinoethyl)pyrazine (0.87 g) was added portionwise to a stirred suspension of sodium hydride (0.25 g) in DMF (20 ml) at approximately 5° C. After 1 hour a solution of (E)-methyl 2-[2-(bromomethyl)phenyl]-3-methoxypropenoate (1.5 g) in DMF (5 ml) was added to the reaction mixture at 0° C. After 1½ hours the mixture was poured into water and extracted (×2) with ether. The combined extracts were washed with brine, then dried, concentrated and chromatographed using ether:hexane 1:1 as the eluant, to give the title compound, a mixture of oxime isomers (major:minor 7:3), as a pale pink solid (0.57 g, 30% yield) m.p. 56°–60° C.

IR maxima (film): 1707, 1624, 1132 cm$^{-1}$. $^1$H NMR (270 MHz) major isomer- δ: 2.39(3H,s), 2.54(3H,s), 2.57(3H,s), 3.67(3H,s), 3.82(3H,s), 5.15(2H,s), 7.1–7.9(4H,m), 7.59(1H,s), 8.27(1H,s) ppm. Minor isomer- δ: 2.22(3H,s), 2.51(3H,s), 2.57(3H,s), 3.67(3H,s), 3.82(3,Hs), 5.27(2H,s), 7.1–7.9(4H,m), 7.76(1H,s), 8.33(1H,s) ppm.

EXAMPLE 3

This Example illustrates the preparation of (E), (E)-methyl 3-methoxy-2-[2-(phenylacetoximinomethyl)phenyl]propenoate (Compound No. 23 of Table I).

A solution of acetophenone oxime (1.23 g) in DMF (5 ml) was added dropwise to a stirred suspension of sodium hydride (0.367 g) in DMF (25 ml). After 1 hour, a solution of (E)-methyl 2-[2-(bromomethyl)phenyl]-3-methoxypropenoate (2.0 g) in DMF (15 ml) was added to the reaction mixture, which was then stirred at room temperature for 16 hours. The mixture was poured into water and extracted (×2) with ether. The combined extracts were washed with water, then dried, concentrated and chromatographed using ether: 40–60 petroleum 3:2 to give a crude oil. HPLC using ether: 40–60 petroleum 1:1 gave the title compound (0.55 g, 23% yield) as a pale yellow oil.

IR maxima (film):1708, 1631 cm$^{-1}$. $^1$H NMR given in Table II.

EXAMPLE 4

This Example illustrates the preparation and separation of the (E),(E)- and (Z),(E)-isomers of methyl 3-methoxy-2-{2-[(pyrimidin-5-ylisopropyloximino)-0-methyl]phenyl}propenoate (Compounds Nos. 66 and 67 of Table I).

A solution of the oxime of isopropylpyrimidin-5-yl ketone (0.29 g of a 3:2 mixture of the (E)-: (Z)-isomers) in DMF (5 ml) was added to a stirred suspension of sodium hydride (0.09 g) in DMF (10 ml). After 2 hours the mixture was cooled to 0° C. and a solution of (E)-methyl 2-[2-(bromomethyl)phenyl]-3-methoxypropenoate (0.5 g) in DMF (5 ml) was added to the reaction mixture, which was then stirred for 3 hours. The mixture was poured into water and extracted with ether. The combined extracts were washed with water, then dried and concentrated to give an oil, the crude mixture of (E),(E)- and (Z),(E)-isomers. HPLC using ether as the eluant was used to separate these isomers into their two components:

1. The faster eluting fraction- the (Z)-oxime ether, (E)-propenoate. (0.115 g, 18% yield). A clear oil. (Compound No. 67 of Table I).
2. The slower eluting fraction- the (E)-oxime ether, (E)-propenoate. (0.098 g 15% yield). A clear oil (Compound No. 66 Table I).

$^1$H NMR given in Table II.

EXAMPLE 5

This Example illustrates the preparation of one stereoisomer of methyl 2-[2-(phenyl[methylthio]oximinomethyl)phenyl]-3-methoxypropenoate (Compound No. 191 of Table I).

A solution of chlorine (1.5 g) in carbon tetrachloride (42 ml) was added in portions to a stirred partial solution of benzaldehyde oxime [2.5 g; $^1$H NMR: δ8.18(1H,s), 9.40(1H,brs) ppm] in carbon tetrachloride (20 ml) at room temperature. Following the addition, the reaction mixture was stirred at room temperature for 3 hours then poured into water. The organic layer was separated, dried and concentrated to give almost pure α-chlorobenzaldehyde oxime (3.2 g) as a yellow liquid. A solution of sodium methanethiolate (0.68 g) in methanol (15 ml) was added dropwise to an ice-cooled and stirred solution of part of this α-chlorobenzaldehyde oxime (1.5 g) in methanol (15 ml). Following the addition, the reaction mixture was stirred for 2 hours with continued cooling in iced-water. The methanol was removed under reduced pressure and the residue was chromatographed using dichloromethane as eluant to give a single stereoisomer of α-methylthiobenzaldehyde oxime (0.670 g, 42% yield) as a white crystalline solid, m.p. 76°–78° C., $^1$H NMR: δ2.08(3H,s), 9.12(1H,s) ppm.

A solution of α-methylthiobenzaldehyde oxime (0.575 g) in DMF (10 ml) was added dropwise to a stirred suspension of sodium hydride (85 mg) in DMF (15 ml) at room temperature. An hour later, a solution of (E)-methyl 2-[2-(bromomethyl)phenyl]-3-methoxypropenoate (0.990 g) in DMF was added dropwise and after a further 3 hours the mixture was poured into water and extracted with ethyl acetate. The organic extracts were washed with water, dried, concentrated and chromatographed using increasing proportions of ethyl acetate in hexane as eluant to give the title compound (1.05 g, 83%) as a colourless oil, IR: 1706 cm$^{-1}$.

$^1$H NMR given in Table II.

EXAMPLE 6

This Example illustrates the preparation of single stereoisomers of methyl 2-[2-(phenyl[methylsulphinyl]oximinomethyl)phenyl]-3-methoxypropenoate and methyl 2-[2-(phenyl[methylsulphonyl]oximinomethyl)phenyl]-3-methoxypropenoate (Compound Nos. 227 and 228 of Table I). m-Chloroperbenzoic acid (0.250 g, containing 45% m-chlorobenzoic acid) was added in portions during 30 minutes to a stirred solution of methyl 2-[2-(phenyl[methylthio]oximinomethyl)phenyl]-3-methoxypropenoate (0.300 g, prepared as described in Example 5) in dichloromethane (20 ml) cooled in iced-water. After a further 15 minutes, the reaction mixture was washed successively with aqueous sodium bicarbonate and water then dried, concentrated and chromatographed using a 1:1 mixture of ethyl acetate and hexane as eluant to give the title compounds: (i) the sulphone, eluted first, as a gum (0.090 g, 28% yield); and (ii) the sulphoxide, also a gum (0.150 g, 48% yield).

$^1$H NMR given in Table II.

EXAMPLE 7

This Example illustrates the preparation of two stereoisomers of methyl 2-[2-(phenyl-[methoxy]oximinomethyl)phenyl]-3-methoxypropenoate (Compound Nos. 225 and 226 of Table I).

A mixture of stereoisomers of α-methoxybenzaldehyde oxime was prepared in 2 steps from methyl benzoate by successive treatment with Lawesson's reagent and hydroxylamine (see, for example, EP 0 299 382). The stereoisomers were separated by chromatography using dichloromethane as eluant:

(i) Isomer A, eluted first, a pale yellow solid, m.p. 55°–57° C., $^1$H NMR: δ3.83(3H,s), 7.72(1H,s) ppm; and (ii) Isomer B, a colourless gum, $^1$H NMR: δ3.96(3H,s), 8.84(1H,s) ppm.

These 2 stereoisomeric oximes were converted individually into the title compounds by the method described in Example 5, that is by successive treatment with sodium hydride and (E)-methyl 2-[2-(bromomethyl)phenyl]-3-methoxypropenoate. Isomer A gave the title compound No. 225 of Table I as a gum; isomer B gave the title compound no. 226 of Table I, also a gum.

$^1$H NMR given in Table II.

The following are examples of compositions suitable for agricultural and horticultural purposes which can be formulated from the compounds of the invention. Such compositions form another aspect of the invention. Percentages are by weight.

EXAMPLE 8

An emulsifiable concentrate is made up by mixing and stirring the ingredients until all are dissolved.

| | |
|---|---|
| Compound No. 45 of Table I | 10% |
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 9

The active ingredient is dissolved in methylene dichloride and the resultant liquid sprayed on to the granules of attapulgite clay. The solvent is then allowed to evaporate to produce a granular composition.

| | |
|---|---|
| Compound No. 45 of Table I | 5% |
| Attapulgite granules | 95% |

EXAMPLE 10

A composition suitable for use as a seed dressing is prepared by grinding and mixing the three ingredients.

| | |
|---|---|
| Compound No. 45 of Table I | 50% |
| Mineral oil | 2% |
| China clay | 48% |

EXAMPLE 11

A dustable powder is prepared by grinding and mixing the active ingredient with talc.

| | |
|---|---|
| Compound No. 45 of Table I | 5% |
| Talc | 95% |

EXAMPLE 12

A suspension concentrate is prepared by ball milling the ingredients to form an aqueous suspension of the ground mixture with water.

| | |
|---|---|
| Compound No. 45 of Table I | 40% |
| Sodium lignosulphonate | 10% |
| Bentonite clay | 1% |

| -continued | |
|---|---|
| Water | 49% |

This formulation can be used as a spray by diluting into water or applied directly to seed.

EXAMPLE 13

A wettable powder formulation is made by mixing together and grinding the ingredients until all are thoroughly mixed.

| | |
|---|---|
| Compound No. 45 of Table I | 25% |
| Sodium lauryl sulphate | 2% |
| Sodium lignosulphonate | 5% |
| Silica | 25% |
| China clay | 43% |

EXAMPLE 14

The compounds were tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace-5% of disease on untreated plants
2=6-25% of disease on untreated plants
1=26-59% of disease on untreated plants
0=60-100% of disease on untreated plants
The results are shown in Table III.

TABLE III

| COMPOUND NO. | TABLE NO. | PUCCINIA RECONDITA (WHEAT) | ERYSIPHE GRAMINIS HORDEI (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS (TOMATO) |
|---|---|---|---|---|---|---|---|---|
| 1 | I | — | 3 | 4 | 4 | 4 | 4 | 4 |
| 2 | I | 4 | 4 | 4 | 4 | 4 | 4 | 3 |
| 5 | I | 4 | 4 | 4 | — | 4 | 4 | 3 |
| 6 | I | — | 4 | 4 | 3 | 4 | 4 | 3 |
| 11 | I | 4 | 4 | 4 | — | 4 | 4 | 3 |
| 17 | I | 4 | 4 | 4 | — | 4 | 4 | 3 |
| 20 | I | 4 | 4 | 4 | — | 4 | 4 | 3 |
| 22 | I | 3 | 4 | 4 | — | 4 | 4 | 4 |
| 23 | I | 4 | 1 | 4 | 4 | 4 | 4 | 1 |
| 29 | I | 3 | 4 | 4 | — | 4 | 4 | 3 |
| 32 | I | 4 | 4 | 4 | — | 4 | 4 | 4 |
| 37 | I | 3 | 0 | 0 | — | 4 | 0 | 0 |
| 38 | I | 4 | 4 | 4 | — | 2 | 4 | 0 |
| 39 | I | 3 | 4 | 4 | 0 | — | 4 | 4 |
| 40 | I | 3 | 0 | 2 | — | 3 | 2 | 3 |
| 41 | I | — | 4 | 4 | 0 | — | 4 | 2 |
| 42 | I | 1 | 0 | 4 | — | — | 4 | 4 |
| 45 | I | 3 | 4 | 4 | 4 | 2 | 4 | 0 |
| 47 | I | 3 | 0 | 4 | — | 2 | 4 | 4a |
| 49 | I | 0 | 0 | 4a | 3a | 4a | 4a | 4 |
| 55 | I | 4a | 4a | 4 | 4 | — | 4 | 4 |
| 62 | I | 4 | 4 | 4 | 3 | 4 | 4 | 0 |
| 63 | I | 4 | 4 | 4 | 3 | 4 | 4 | 0 |
| 64 | I | 4 | 4 | 0 | 0 | 2 | 4 | 0 |
| 65 | I | 4 | 3 | 4 | 0 | 3 | 4 | 4 |
| 66 | I | — | 4 | 0 | 4 | 4 | 4 | 2 |
| 67 | I | 4 | 4a | 4a | 0a | 4a | 4a | 0a |
| 89 | I | 4a | 4 | 3 | — | — | 4 | 4 |
| 90 | I | 3 | 2 | 3 | 3 | 4 | 3 | 3 |
| 92 | I | 4 | 4 | 4 | — | — | 4 | 4 |
| 93 | I | 4 | 4 | 3 | 3 | — | 4 | 2 |
| 101 | I | 4 | 3 | 3 | 3 | — | 0 | 0 |
| 110 | I | 4 | 3 | 4 | 4 | — | 4 | 4 |
| 112 | I | 4 | 4 | 0 | — | 4 | 0 | 0 |
| 113 | I | 4 | 4 | 4 | 3 | — | 4 | 4 |
| 116 | I | 3 | 3 | 4 | 3 | — | 4 | 2 |
| 121 | I | 4 | 4 | 4 | 4 | 4 | 4 | 0 |
| 125 | I | 3 | 4 | 4 | 0 | 4 | 0 | 3 |
| 127 | I | 4a | 4 | 0 | 3 | 4 | 4 | 0 |
| 130 | I | 4 | 4 | 4 | 4 | — | 4 | 4 |
| 139 | I | 2 | 0 | 2 | 0 | 2 | 0 | 2 |
| 140 | I | 4 | 4 | 4 | 4 | 2 | 4 | 0 |
| 143 | I | 4 | 4 | 4 | 0 | 4 | 4 | 3 |
| 144 | I | 2 | 4 | 4 | 3 | 2 | 4 | 0 |
| 152 | I | 4 | 4 | 4 | 3 | 4 | 4 | 3 |
| 153 | I | 4 | 4 | 4 | 3 | 4 | 4 | 3 |
| 154 | I | 3 | 4 | 4 | — | 3 | 4 | 4 |
| 156 | I | 2 | 4 | 4 | 0 | 3 | 4 | 3 |
| 157 | I | 3 | 4 | 4 | 2 | 3 | 4 | 4 |

TABLE III-continued

| COMPOUND NO. | TABLE NO. | PUCCINIA RECONDITA (WHEAT) | ERYSIPHE GRAMINIS HORDEI (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYYOPHTHORA INFESTANS (TOMATO) |
|---|---|---|---|---|---|---|---|---|
| 158 | I | 4 | 3 | 4 | 2 | 3 | 4 | 4 |
| 159 | I | 4 | 4 | 4 | 2 | 3 | 0 | 0 |
| 162 | I | 4 | 4 | 4 | 4 | 4 | 4 | 3 |
| 165 | I | 0 | 0 | 0 | — | 1 | 0 | 0 |
| 173 | I | 4 | 4 | 4 | 0 | 4 | 4 | 0 |
| 174 | I | 4 | — | 4 | 3 | 4 | 4 | 3 |
| 175 | I | 4 | 4 | 4 | 4 | 4 | 4 | 3 |
| 176 | I | 4 | 4 | 4 | 4 | 4 | 4 | 3 |
| 177 | I | 4 | 4 | 4 | 4 | 4 | 4 | 3 |
| 183 | I | 3a | 3a | 3a | 0a | 4a | 4a | 3a |
| 184 | I | 4 | 4 | 4 | 2 | 4 | 4 | 4 |
| 185 | I | 4 | 4 | 4 | — | — | 4 | 2 |
| 186 | I | 4a | 4a | 4a | — | — | 4a | 0a |
| 188 | I | 4 | 4 | 4 | 4 | — | 4 | 4 |
| 194 | I | 4 | 0 | 4 | 4 | — | 4 | 4 |

(—) No result, (a) 10 ppm foliar spray only

EXAMPLE 15

The insecticidal properties of the compound of formula (I) were demonstrated as follows:

The activity of the compound was determined using a variety of insect, mite and nematode pests. Except in the case of knockdown activity against *Musca domestica*, where the test procedure is described later, the compound was used in the form of liquid preparations containing from 12.5 to 1000 parts per million (ppm) by weight of the compound. The preparations were made by dissolving the compound in acetone and diluting the solutions with water containing 0.1% by weight of a wetting agent sold under the trade name "SYNPERONIC" NX until the liquid preparations contained the required concentration of the product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to seven days after the treatment.

The results of the tests are shown in Table IV for each of the compounds in the first column and at the rate in parts per million given in the second column. They are shown as a grading of mortality designated as 9, 5 or 0, wherein 9 indicates 80–100% mortality (70–100% root-knot reduction as compared with untreated plants for *Meloidogyne incognita* semi in vitro test), 5 indicates 50–79% mortality (50–69% root-knot reduction for *Meloidogyne incognita* semi in vitro test) and 0 indicates less than 50% mortality.

In Table IV the pest organism used is designated by a letter code. The meaning of the code, the support medium or food, and the type and duration of test is given in Table V.

The knockdown properties against *Musca domestica* were demonstrated as follows.

A sample of the compound was diluted in 0.1% ethanol/acetone (50:50 mixture) and made up to 1000 ppm solution with 0.1% aqueous Synperonic NX solution. The solution (1 ml) was then sprayed directly onto ten mixed sex houseflies held in a drinking cup containing a sugar lump which was also sprayed.

Immediately after spraying the cups were inverted and left to dry. An assessment of knockdown was made when the cups were righted 15 minutes later. The flies were then provided with a damp cotton wool pad, and held for 48 hours in a holding room conditioned at 25° C. and 65% relative humidity before a mortality assessment was made.

TABLE IV

| COMPOUND NO | RATE (PPM) | TU AC | TU EO | TU NG | MP MC | NC NC | NC NG | MD AK | MD AC | BG NK | BG NC | HV LR | HV LG | SP LR | SP LG | DB LR | MI JC |
|---|---|---|---|---|---|---|---|---|---|---|---|---|---|---|---|---|---|
| 20 | 1000 | 9 | 0 | 0 | 0 | 0 | 0 | 9 | 9 | 0 | 0 | 0 | 0 | 5 | 5 | 0 | |
|  | 25 | | | | | | | | | | | | | | | | 0 |
| 22 | 1000 | 0 | 0 | 0 | 0 | 5 | 9 | 0 | 0 | 0 | 0 | 0 | 0 | 0 | 0 | 0 | |
|  | 25 | | | | | | | | | | | | | | | | 0 |
| 29 | 1000 | 9 | 0 | 0 | 0 | 0 | 0 | 0 | 0 | 0 | 0 | 0 | 0 | 0 | 0 | 9 | |
|  | 25 | | | | | | | | | | | | | | | | 0 |
| 32 | 500 | 0 | 0 | 0 | 0 | 0 | 0 | 0 | 0 | 5 | 5 | 0 | 0 | 0 | 0 | 0 | |
|  | 25 | | | | | | | | | | | | | | | | 0 |
| 37 | 1000 | 0 | 0 | 0 | 0 | 0 | 9 | 0 | 0 | 0 | 0 | 0 | 0 | | | 9 | |
|  | 25 | | | | | | | | | | | | | | | | 0 |
| 38 | 1000 | 5 | 0 | 0 | 0 | 0 | 0 | 0 | 0 | 0 | 0 | 0 | 0 | | | 0 | |
|  | 25 | | | | | | | | | | | | | | | | 0 |
| 40 | 1000 | 0 | 0 | 0 | 9 | 9 | | 9 | 9 | 0 | 0 | 0 | 9 | 0 | 0 | 5 | |
|  | 25 | | | | | | | | | | | | | | | | 0 |
| 42 | 1000 | 9 | 0 | 5 | 0 | 0 | 0 | 0 | 0 | 0 | 0 | 0 | 0 | 0 | 0 | 0 | |
|  | 25 | | | | | | | | | | | | | | | | 0 |
| 47 | 500 | | | | 0 | 5 | 9 | 0 | 0 | 0 | 0 | 0 | 0 | 0 | 0 | 0 | |
| 49 | 1000 | 0 | 0 | 0 | 0 | 9 | | 0 | 0 | 0 | 0 | 0 | 0 | 0 | 0 | 0 | |
|  | 25 | | | | | | | | | | | | | | | | 0 |
| 62 | 500 | | | | 0 | 0 | 0 | 0 | 5 | 0 | 0 | 0 | 0 | 0 | 0 | 0 | |
| 63 | 500 | 0 | 0 | 0 | 5 | 0 | 9 | 9 | 9 | 0 | 0 | 0 | 0 | 0 | 0 | 5 | |
|  | 12.5 | | | | | | | | | | | | | | | | 0 |
| 64 | 500 | 5 | 0 | 0 | 5 | 0 | 0 | 9 | 9 | 0 | 0 | 0 | 0 | 0 | 0 | 5 | |
|  | 12.5 | | | | | | | | | | | | | | | | 0 |
| 89 | 00 | 0 | 0 | 0 | 0 | 5 | 9 | 5 | 9 | 0 | 0 | 0 | 0 | 0 | 0 | 9 | |
|  | 12.5 | | | | | | | | | | | | | | | | 0 |
| 93 | 500 | | | | 0 | 0 | 0 | 0 | 0 | 0 | 0 | 9 | | 0 | 0 | 0 | |
| 101 | 500 | | | | 0 | 0 | 0 | 0 | 5 | 0 | 0 | 0 | 5 | | | 0 | |
|  | 12.5 | | | | | | | | | | | | | | | | 0 |
| 112 | 500 | | | | 9 | 5 | 5 | 0 | 0 | 0 | 0 | 0 | 0 | | | 9 | |
|  | 12.5 | | | | | | | | | | | | | | | | 0 |
| 125 | 500 | | | | 0 | 0 | 0 | 5 | 9 | 0 | 0 | 0 | 0 | | | 0 | |
|  | 12.5 | | | | | | | | | | | | | | | | 0 |
| 140 | 500 | | | | | 9 | | 0 | 0 | 0 | 0 | 0 | 0 | 0 | 0 | 0 | |
| 144 | 500 | | | | 0 | 0 | 0 | 0 | 0 | 0 | 0 | 0 | 9 | 0 | 0 | 9 | |
| 152 | 500 | 0 | 0 | 0 | 0 | 5 | 0 | 0 | 0 | 0 | 0 | 0 | 0 | 0 | 0 | 0 | |
|  | 12.5 | | | | | | | | | | | | | | | | 0 |
| 153 | 500 | | | | 0 | 9 | | 0 | 0 | 0 | 0 | 9 | | | | 0 | |
|  | 12.5 | | | | | | | | | | | | | | | | 0 |
| 157 | 500 | | | | 5 | 0 | 9 | 0 | 0 | 0 | 0 | 0 | 0 | 0 | 0 | 9 | |
| 158 | 500 | | | | 0 | 0 | 5 | 0 | 0 | 0 | 0 | 0 | 9 | 0 | 0 | 0 | |
| 159 | 500 | | | | 9 | 9 | | 0 | 0 | 0 | 0 | 0 | 5 | 5 | 5 | 9 | |
| 160 | 500 | | | | 5 | 0 | 0 | 9 | 0 | 0 | 0 | 0 | 0 | | | 0 | |
|  | 12.5 | | | | | | | | | | | | | | | | 0 |
| 174 | 500 | | | | 0 | 0 | 0 | 9 | 9 | 0 | 5 | 0 | 9 | | | 9 | |
|  | 12.5 | | | | | | | | | | | | | | | | 0 |

TABLE IV-continued

| COMPOUND NO | RATE (PPM) | TU AC | TU EO | TU NG | MP MC | NC NC | NC NG | MD AK | MD AC | BG NK | BG NC | HV LR | HV LG | SP LR | SP LG | DB LR | MI JC |
|---|---|---|---|---|---|---|---|---|---|---|---|---|---|---|---|---|---|
| 175 | 500 |  |  |  | 0 | 0 | 0 | 0 | 5 | 0 | 0 | 0 | 0 |  | 5 |  |  |
|  | 12.5 |  |  |  |  |  |  |  |  |  |  |  |  |  |  |  | 0 |
| 176 | 500 |  |  |  | 0 | 0 | 0 | 9 | 9 | 0 | 0 | 0 | 0 |  | 0 |  |  |
|  | 12.5 |  |  |  |  |  |  |  |  |  |  |  |  |  |  |  | 0 |
| 177 | 500 |  |  |  | 0 | 0 | 0 | 5 | 0 | 0 | 0 | 0 | 0 |  | 5 |  |  |
|  | 12.5 |  |  |  |  |  |  |  |  |  |  |  |  |  |  |  | 0 |

TABLE V

| CODE LETTERS (TABLE IV) | TEST SPECIES | SUPPORT MEDIUM/FOOD | TYPE OF TEST | DURATION (DAYS) |
|---|---|---|---|---|
| TU AC | *Tetranychus urticae* (spider mite - adult) | French bean leaf | Contact | 3 |
| TU EO | *Tetranychus urticae* (spider mite - egg) | French bean leaf | Contact | 3 |
| TU NG | *Tetranychus urticae* (spider mite - nymph) | French bean leaf | Contact (growth) | 6 |
| MP MC | *Myzus persicae* (aphid) | Chinese Cabbage leaf | Contact | 3 |
| NC NC | *Nephotettix cincticeps* (green leaf hopper - nymph) | Rice plant | Contact | 2 |
| NC NG | *Nephotettix cincticeps* (green leaf hopper - nymph) | Rice plant | Contact (growth) | 6 |
| MD AK | *Musca domestica* (housefly - adult) | Plastic pot | Contact (knock-down) | 15 mins |
| MD AC | *Musca domestica* (housefly - adult) | Plastic pot | Contact | 3 |
| BG NK | *Blattella germanica* (cockroach nymph) | Plastic pot | Contact (knock-down) | 15 mins |
| BG NC | *Blattella germanica* (cockroach nymph) | Plastic pot | Contact | 2 |
| HV LR | *Heliothis virescens* (tobacco budworm - larva) | Cotton leaf | Residual | 2 |
| HV LG | *Heliothis virescens* (tobacco budworm - larva) | Cotton leaf | Residual (growth) | 5 |
| SP LR | *Spodoptera exigua* (lesser armyworm - larva) | Cotton leaf | Residual | 2 |
| SP LG | *Spodoptera exigua* (lesser armyworm - larva) | Cotton leaf | Residual (growth) | 5 |
| DB LR | *Diabrotica balteata* (cucumber beetle - larva) | Filter paper/ maize seed | Residual | 2 |
| MI JC | *Meloidogyne incognita* (rootknot nematode - larva) | in vitro | Contact | 1 |

"Contact" test indicates that both pests and medium were treated and "Residual" indicates that the medium was treated before infestation with the pests.

We claim:

1. A compound of the formula

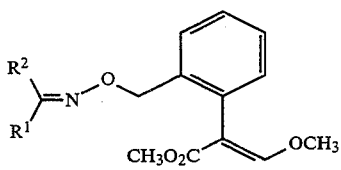

where $R^1$ is phenyl or phenyl substituted with a $CF_3$ group and $R^2$ is hydrogen or lower alkyl.

2. A compound according to claim 1 wherein $R^2$ is methyl.

3. A compound according to claim 1 wherein $R^1$ is 3-$CF_3$-phenyl and $R^2$ is hydrogen or methyl.

4. A fungicidal, insecticidal or miticidal composition comprising, as an active ingredient, a compound as defined in claim 1 and a fungicidally, insecticidally or miticidally acceptable carrier or diluent therefor.

5. A process for combating fungi which comprises applying to a plant, to a seed of a plant or to the locus thereof, a fungicidally effective amount of a compound as claimed in claim 1.

6. A process for killing or controlling insects or mites which comprises administering to the insect or mite or to the locus thereof an insecticidally or miticidally effective amount of a compound as claimed in claim 1.

* * * * *